United States Patent [19]

Bauman et al.

[11] 4,060,620

[45] Nov. 29, 1977

[54] INDUCTION OF LACTATION IN NONPREGNANT DAIRY ANIMALS

[75] Inventors: Dale E. Bauman, St. Joseph, Ill.; Robert J. Collier, East Lansing, Mich.; Ray L. Hays, Champaign, Ill.

[73] Assignee: University of Illinois Foundation, Urbana, Ill.

[21] Appl. No.: 687,205

[22] Filed: May 17, 1976

[51] Int. Cl.² .............................................. A61K 31/475
[52] U.S. Cl. ..................................................... 424/262
[58] Field of Search ......................................... 424/262

[56] References Cited

PUBLICATIONS

Yamanouchi et al. – Chem. Abst., vol. 82 (1975) p. 119342w.

Primary Examiner—Sam Rosen
Attorney, Agent, or Firm—Fidelman, Wolffe & Waldron

[57] ABSTRACT

The administration of reserpine to nonlactating dairy cattle produces a marked increase in circulating serum prolactin levels. The parenteral administration of reserpine to nonlactating cows which have been hormonally induced into lactation, as by the parenteral administration of an estrogen and progesterone, and dexamethasone, results in a substantial rise in milk production.

12 Claims, No Drawings

INDUCTION OF LACTATION IN NONPREGNANT DAIRY ANIMALS

BACKGROUND OF THE INVENTION

The present invention relates to a novel method for producing lactogenesis in nonpregnant dairy animals.

It is known that prolactin, a hormone produced by the anterior lobe of the pituitary gland, is an essential factor in initiating and sustaining lactation in mammals, and that its action depends upon the presence of other essential hormones such as estrogens, progesterone and oxytocin.

In 1971, there was described the use of 17$\beta$-estradiol and progesterone to induce lactation in nonpregnant dairy cows, wherein subcutaneous injections were administered twice daily of 17$\beta$ estradiol (0.1 mg/kg body weight per day), and progesterone (0.25 mg/kg body weight per day), during a period of 1 to 7 days; Smith et al., J. Dairy Sci., 54:1886 (1971). While successful lactation occurred in some cows with this treatment, a substantial number of animals failed to lactate or produced only a very limited amount of milk. It is possible that the failure of the nonlactating group might have been the absence of prolactin as a component of the lactogenic complex, since it is known that serum prolactin levels increase dramatically approximately 2 days prepartum in pregnant dairy animals; Convey, J. Dairy Sci., 57: 905–917 (1974).

The availability of prolactin per se is so limited that its use for potentiating hormonal induction of lactation in dairy animals is impractical. However, a number of other compounds such as prostaglandins, thyrotropin releasing hormone (TRH), serotonin and many psychoactive drugs stimulate prolactin release: Clemens and Meites, Lactogenic Hormones, pp. 111–142 (1974); Louis et al., Proc. Soc. Exp. Biol. Med. 147: 128–133 (1974); Tucker et al., ibid, 149: 462–469 (1975). Most of these compounds either result in a prolactin release lasting only a few minutes or cause the release of both prolactin and thyroxine, which latter substance may inhibit the lactogenic role of prolactin.

The use of reserpine, an ester alkaloid derived from the roots of *Rauwolfia serpentina*, to induce lactation in pregnant animals via prolactin release is known. Thus reserpine injections produce prolonged release of prolactin in rats and rabbits: Kanematsu et al., Proc. Soc. Ex. Biol. Med., 113: 967–974 (1963); Meites, ibid., 96: 728–731 (1957); Meites et al., ibid. 101: 563–565 (1959).

Bass et al., Arch. int. de Pharmacodynamie et de Therapie, 211: 188–192 (1974) studied the effect of administering various known prolactin releasers, including reserpine, to lactating ewes during the fourth month of lactation when milk yield has fallen to less than 50%, thus indicating lack of endogenous prolactin. Of 14 compounds tested, only five yielded a significant increase in milk yield during treatment (6 days) which faded when injections were stopped, and reserpine was not among these five. The reserpine was found to produce a syndrome including diarrhoea, loss of appetite, and prostration.

The oral administration of reserpine and analogous substances derived from Rauwolfia plants, to livestock, poultry, pigs and the like, by inclusion in animal feeds is disclosed in U.S. Pat. No. 3,092,496, where Rauwolfia root is said to be a growth stimulant, and in U.S. Pat. No. 3,178,340 for its tranquilizing effect.

GENERAL DESCRIPTION OF THE INVENTION

In accordance with the present invention, there is provided a novel method for the induction of lactation in nonpregnant, nonlactating dairy animals, particularly bovine animals.

It has been found, surprisingly and unexpectedly, that the parenteral, and particularly the intramuscular administration of reserpine and like substances to nonlactating dairy cattle (cows) produces a marked increase in circulating serum prolactin levels for periods of 6 to 8 hours and more.

It was further found, in accordance with the invention, that the administration of reserpine and like substances to nonlactating cows which have been hormonally inducted into lactation, results in a substantial rise in milk yield.

The parenteral administration of reserpine to nonpregnant cattle has not, as far as known, been previously described.

Without relying on any particular theory, it is believed that the action of the reserpine arises from its interference with the physiological effects of dopamine in the hypothalamicpituitary axis by depletion of dopamine, inhibition of dopamine binding, or inhibition of dopamine synthesis, thereby resulting in pituitary prolactin release.

Reserpine and its pharmaceutically acceptable salts may be employed in the practice of the invention, which will be illustrated with respect to reserpine per se, it being understood however that the practice of the invention is not to be regarded as limited thereto.

Among the salts of reserpine which may be employed are the hydrochloride, sulfate, nitrate, perchlorate, maleate, and picrate.

The reserpine or its salts are administered parenterally, preferably intramuscularly, in a dosage range per animal between about 2 mg to about 7 mg reserpine content, with 5 mg being preferred.

For the induction of lactation, there are administered parentally an estrogen and progesterone, the preferred estrogen being 17$\beta$-estradiol. There may be optionally administered a glucocorticoid steroid, such as, for example, dexamethasone (9-fluoro-11$\beta$, 17, 21-trihydroxy-16$\alpha$-methylpregna-1,4-diene-3,20-dione). The use of dexamethasone for preventing retention of placenta following induced parturition in cattle by parenteral administration to pregnant cows, is disclosed in U.S. Pat. No. 3,775,539.

In accordance with the presently preferred practice of the invention, nonpregnant ruminants, such as cows, ewes, or goats, are hormonally induced to lactate with daily subcutaneous injections of an estrogen, such as 17$\beta$-estradiol, and progesterone on days 1 to 7 of the treatment.

The estrogen concentration may range between about 0.5 and about 2.0 mg/kg of body weight, with 0.1 mg being preferred. The concentration of progesterone ($\Delta^4$-pregnene-3,20-dione) may range between about 0.10 and about 0.50 mg/kg, with 0.25 being preferred. The concentration of dexamethasone may, if used, range from about 15 to about 30 mg per day.

The reserpine is administered via intramuscular injection in the hip region on days succeeding the hormone administration, for example, as a series on days 13, 14, 15 and 16, or as a series on alternate days 8, 10, 12 and 14.

DETAILED DESCRIPTION OF THE INVENTION

The practice of the invention will be better understood by reference to the following examples, which are to be considered as illustrative, and not as limiting.

EXAMPLE 1

Animal Tolerance to Reserpine

Animal tolerance to reserpine was investigated using four cows in late lactation. A single daily injection of 5 mg/day of reserpine (Sandril; Eli Lilly, Indianapolis, IN) was administered intramuscularly in the hip region for 4 consecutive days, or 2 ml of 0.9% NaCl, without reference to stage of estrus cycle.

The effect of reserpine on serum prolactin levels was also investigated with four nonlactating, nonpregnant cows. Each cow was fitted with an indwelling jugular catheter of silastic tubing and the catheter kept open by flushing with a salin-heparin solution. The animal was allowed a 24 hour adjustment period to become accustomed to the investigators and the intermittent drawing of blood samples. A single 5 mg dose of reserpine was given via intramuscular injection in the hip region and blood samples were periodically withdrawn via the jugular catheter for 48 hours. Seventy-two hours following the reserpine injection a 2 ml, 0.9% saline injection was given intramuscularly and the schedule of blood sampling repeated. Blood samples were allowed to equilibrate at room temperature for 4 hours, centrifuged and the serum removed and frozen. Serum prolactin was analyzed using a double-antibody radioimmunoassay.

Prolactin in jugular blood at 0, 0.5, 2, 3, 6, 8 and 12 hr. averaged 27, 196, 276, 304, 246, 183 and 153 ng/ml, respectively, after reserpine; after saline injection prolactin ranged from 18 to 40 ng/ml. For initial investigations in Example 1, 5 mg per day of reserpine was administered via a daily intramuscular injection for 4 consecutive days. Side reactions noted were some labored breathing, nasal congestion and drowsiness on the afternoon following the 3rd and 4th injections. However, there was no trouble in getting animals to stand. In Examples 2 and 3, animals receiving reserpine injections developed identical side reactions. In addition, approximately one-third of the animals had some difficulty in standing on the afternoon of the last reserpine injection. By 48 hours after the last reserpine injection, the side reactions to reserpine were not apparent in any of the animals.

EXAMPLE 2

Control Treatment to Induce Lactation

Seven nonpregnant heifers and cows were used in this study. Cows had at least a 34 day dry period prior to the start of the treatment to induce lactation. All animals were given subcutaneous injections of 17$\beta$ estradiol plus progesterone on days 1 to 7 of the treatment period and intramuscular injections of dexamethasone on days 18 to 20 as previously described. Three of the animals received no additional injections (Control treatment group). Four of the animals were given intramuscular injections (once a day injection in the hip region) of 5 mg/day of reserpine on days 13, 14, 15 and 16 (Reserpine 1 treatment group). Blood samples were obtained periodically throughout the treatment period by tail venipuncture for both groups of animals. Blood samples were handled and serum prolactin analyzed as in Example 1. In Example 2, reserpine was administered on days 13, 14, 15 and 16 of the treatment period. These days were chosen such that the prolactin levels in cows induced into lactation would possibly mimic the increase in serum prolactin which occurs in pregnant cows in the period immediately prior to parturition.

EXAMPLE 3

Hormonal Induction of Lactation Modified by Administration of Reserpine

Eight nonpregnant parous cows were utilized in this study. Cows had been dry for 35 days at the time of the first hormone injection. All cows received the 17$\beta$ estradiol plus progesterone and the dexamethasone injections as indicated in Example 2. Five of the animals also received 5 mg/day of reserpine on days 8, 10, 12 and 14 of the treatment period (Reserpine 11 treatment group). Reserpine was administered via an intramuscular injection in the hip region of the animals. Blood samples were obtained via tail venipuncture on days 0, 6, 9, 10, 15, 17, 19 and 21 of the treatment period and analyzed for prolactin as described in Example 1.

In Example 3 the hormonal treatment to induce lactation in nonpregnant cows was modified with the administration of reserpine on days 8, 10, 12 and 14. The days of reserpine administration for Example 3 were chosen on the basis of information which indicated that mammary tissue from cows successfully induced into lactation was undergoing the cellular changes associated with lactogenesis during the interval between day 8 and day 16 of the treatment period.

Serum prolactin values remained low during the treatment period when 17$\beta$ estradiol plus progesterone injections were administered. In the interval between day 16 and day 21 of the treatment period there was an apparent increase in serum prolactin levels although the variation between animals had increased markedly. This was particularly evident at days 15 to 16. All five control animals averaged 97 ± 59 ng/ml on days 15 and 16, but the omission of one cow with an extremely high serum prolactin concentration lowered the average to 40 ± 17 ng/ml.

The milk production of animals in Examples 2 and 3 is shown in Table 1:

Table 1.

| Milk production of cows hormonally induced into lactation | | | |
|---|---|---|---|
| | Experimental period | | |
| Treatment[a] | Days | Milk yield (kg) | Highest daily milk yield (kg) |
| Control (3) | 100 | 96 ± 163 | 6 (range 4–10) |
| Reserpine I (4) | 100 | 1121 ± 133 | 14 (range 10–16) |
| Control (2) | 100 | 865 ± 78 | 11  5 (range 10–13) |
| Reserpine II (5) | 100 | 1314 ± 75 | 17  5 (range 15–22) |

[a]Control = 17. $\beta$-estradiol + progesterone. Reserpine I = Control treatment + 5 mg reserpine (intramuscular injection) on days 13, 14, 15 and 16. Reserpine II = Control treatment + 5 mg reserpine (intramuscular injection) on days 8, 10, 12 and 14. The number of animals is indicated in parentheses.

In Example 2 the reserpine treated animals had a higher milk yield than the positive controls. Relative to the control group, reserpine treated animals in Example 3 also had a higher milk production for the experimental period. In both studies all of the animals receiving reserpine were successfully induced into lactation using the criterion of success as a peak milk yield greater than 9 kg/day. There were no apparent differences in milk production between the two reserpine groups although the reserpine II treatment group tended to have a greater peak daily milk yield.

What is claimed is:

1. Method for inducing copious milk production in an initially nonpregnant, nonlactating dairy animal which has been hormonally induced into lactation which comprises parenterally administering to said animal after the start of the hormone treatment an effective lactation-increasing amount of reserpine or a pharmaceutically acceptable salt thereof.

2. The method of claim 1 in which said hormonal induction is achieved by the parenteral administration of an effective-lactation inducing amount of an estrogen and progesterone.

3. The method of claim 2 in which said estrogen is 17β-estradiol.

4. The method of claim 2 in which the effective dosage of reserpine is between about 2 mg and about 7 mg per animal.

5. The method of claim 1 in which said dairy animal is a bovine and the yield of milk produced is at least about 9 kg per day.

6. Method for inducing copious milk production in an initially nonpregnant, nonlactating dairy animal which is first hormonally induced into lactation, comprising the steps of:
   a. parenterally administering daily for a period of 1 to 7 days an effective lactation-inducing amount of an estrogen and progesterone; and
   b. parenterally administering during a period of days 8 to 17 thereafter an effective lactation-increasing amount of reserpine or a pharmaceutically acceptable salt thereof.

7. The method of claim 6 in which the reserpine is administered on days 13, 14, 15 and 16.

8. The method of claim 6 in which the reserpine is administered on days, 8, 10, 12 and 14.

9. The method of claim 6 in which there is additionally parenterally administered a therapeutically effective amount of dexamethasone.

10. The method of claim 6 in which the estrogen is 17β-estradiol.

11. The method of claim 6 in which the effective dosage of reserpine is between about 2 mg and about 7 mg per animal.

12. The method of claim 6 in which said dairy animal is a bovine and the yield of milk produced is at least about 9 kg per day.

* * * * *